US012419826B2

(12) United States Patent
Han et al.

(10) Patent No.: US 12,419,826 B2
(45) Date of Patent: Sep. 23, 2025

(54) COSMETIC COMPOSITION FOR IMPROVING FRAGRANCE PERSISTENCE

(71) Applicant: LG HOUSEHOLD & HEALTH CARE LTD., Seoul (KR)

(72) Inventors: Nakyung Han, Seoul (KR); Seungmin Han, Seoul (KR); Ilgu Kim, Seoul (KR); Sun Gyoo Park, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 814 days.

(21) Appl. No.: 17/294,170

(22) PCT Filed: Nov. 15, 2019

(86) PCT No.: PCT/KR2019/015698
§ 371 (c)(1),
(2) Date: May 14, 2021

(87) PCT Pub. No.: WO2020/101446
PCT Pub. Date: May 22, 2020

(65) Prior Publication Data
US 2022/0008318 A1    Jan. 13, 2022

(30) Foreign Application Priority Data

Nov. 15, 2018   (KR) .................. 10-2018-0141102
May 27, 2019    (KR) .................. 10-2019-0062010

(51) Int. Cl.
*A61K 8/87*     (2006.01)
*A61K 8/02*     (2006.01)
*A61K 8/891*    (2006.01)
*A61Q 13/00*    (2006.01)
*A61Q 19/00*    (2006.01)

(52) U.S. Cl.
CPC ........... *A61K 8/87* (2013.01); *A61K 8/0291* (2013.01); *A61K 8/891* (2013.01); *A61Q 13/00* (2013.01); *A61Q 19/00* (2013.01)

(58) Field of Classification Search
None
See application file for complete search history.

(56) References Cited

U.S. PATENT DOCUMENTS

2005/0244442 A1*  11/2005  Sabino .............. A61K 8/26
                                                   424/401
2017/0367965 A1   12/2017  Bouchard

FOREIGN PATENT DOCUMENTS

| JP | 2010-513369 A     | 4/2010 | |
|----|-------------------|--------|---|
| JP | 2016-88868 A      | 5/2016 | |
| KR | 10-2004-0029424 A | 4/2004 | |
| KR | 10-2011-0037911 A | 4/2011 | |
| KR | 10-2012-0043194 A | 5/2012 | |
| KR | 10-2013-0113965 A | 10/2013 | |
| KR | 10-2017-0063205 A | 6/2017 | |
| KR | 10-2018-0004823 A | 1/2018 | |
| KR | 10-2018-0005256 A | 1/2018 | |
| KR | 10-2018-0036292 A | 4/2018 | |
| WO | WO-2016096928 A1 * | 6/2016 | ............... A61K 8/34 |
| WO | WO-2017018541 A1 * | 2/2017 | ............... A61K 8/19 |

OTHER PUBLICATIONS

Dow Corning Aculyn 44 Product Sheet, https://dokumen.tips/documents/aculyn-44-rheology-modifierstabilizer-an-anti-acne-benzoyl-peroxidelotions.html?page=7, Apr. 2004 (Year: 2004).*
Yuan et al., Multiscale Molecular Dynamics Simulations of Model Hydrophobically Modified Ethylene Oxide Urethane Micelles, J. Phys. Chem. B 2015, 119, 12540-12551 (Year: 2015).*
The office action issued in corresponding Japanese Application No. 2021-526342, 4 pages, mailed Jun. 6, 2022.
Signature Special Set: Vonin the Character: Black, LG Household & Health Care, (ID#):5414709, Mintel GNPD [online] http://www.gnpd.com, Feb. 2018, 8 pages.
Office Action in corresponding JP 2021-526342, issued Oct. 2, 2023, 6 pages.
Karlson, "Hydrophobically Modified Polymers. Rheology and Molecular Associations", Physical Chemistry 1, Lund University, 2002, 66 pages.

* cited by examiner

*Primary Examiner* — Jennifer A Berrios
(74) *Attorney, Agent, or Firm* — Vorys, Sater, Seymour and Pease LLP; Mih Suhn Koh

(57) ABSTRACT

Provided is a method for improving fragrance persistence by applying a composition including, as active ingredients: oil; and non-ionic polymers having hydrophobic substituents at both termini thereof. In the composition of the presently claimed subject matter, the non-ionic polymers having hydrophobic substituents at both termini thereof form a flower micelle structure by capturing oil and a fragrance through the hydrophobic substituents, and thus can stably maintain the oil and fragrance and prevent fast volatilization of the fragrance, thereby improving fragrance persistence.

5 Claims, 1 Drawing Sheet

[FIG. 1]
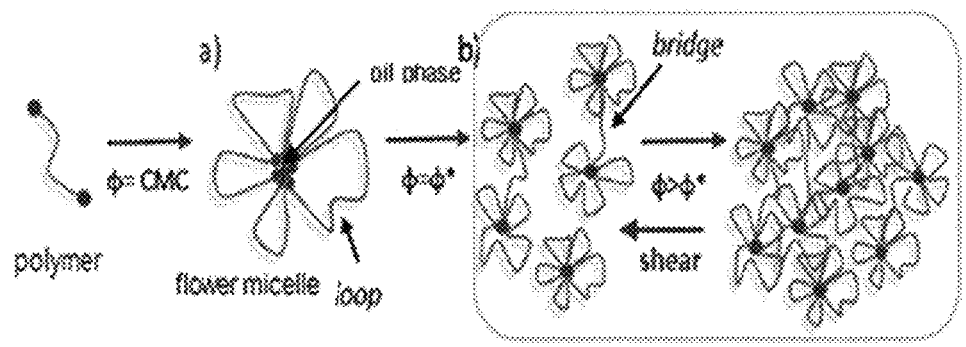
[FIG. 2]
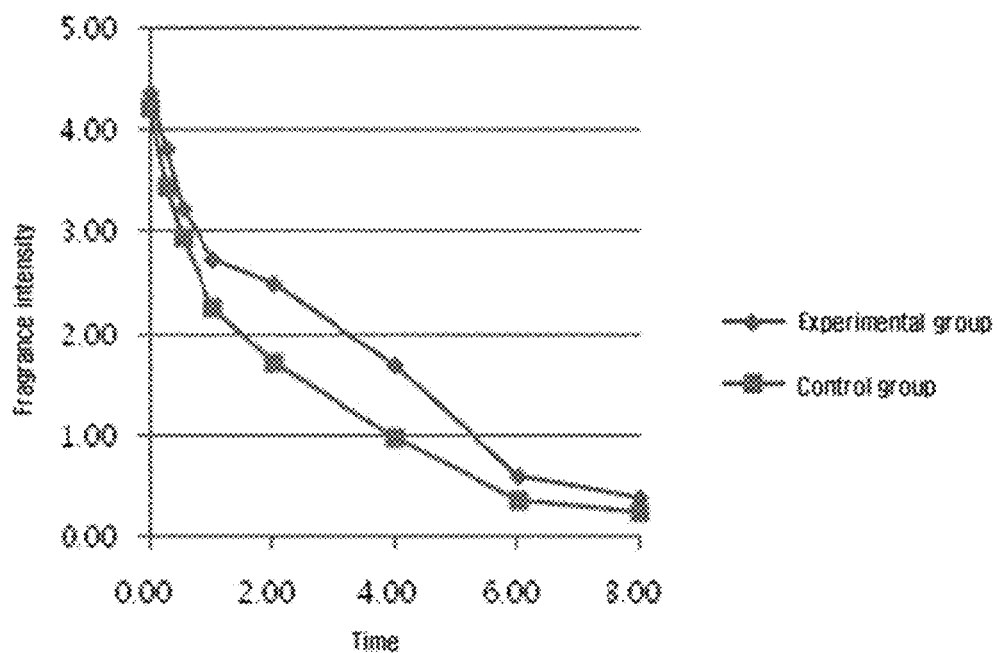

COSMETIC COMPOSITION FOR IMPROVING FRAGRANCE PERSISTENCE

TECHNICAL FIELD

The present invention relates to a cosmetic composition for fragrance persistence containing, as active ingredients, a non-ionic polymer having both-terminal hydrophobic substituents and an oil.

BACKGROUND ART

Recent consumer interview and observation survey results indicate that there will be a growing interest in skin care products that can substitute for perfumes beyond existing fragrant skin care products. Currently, personal fragrance-related new products, such as body mists and perfume body washes, have been released, and overall interest in fragrance is on the increase; for example, perfume brands have diversified, and the market for air fresheners has greatly expanded.

Since the intensity of fragrance generally decreases over time, various attempts have been made to make fragrance persist. In particular, formulations for fragrance persistence have been intensively studied for cleaning and laundry products, pertaining mainly to wash-off products. However, studies on skin care products have been focused only on increasing the stability of fragrance in formulations or increasing persistence of the fragrance itself, and thus, upon the actual application of skin care products, the persistence of fragrance on the skin has been overlooked.

Further, even the studies of fragrance persistence on the skin that have been conducted are merely restricted to cleansing products. Out of these, there are prior studies for increasing fragrance persistence on the skin after washing with a cleansing product employing a polyquaternium (Korean Patent Publication No. 10-2017-0063205: Composition for fragrance persistence and cosmetic composition containing the same), but research is lacking on fragrance persistence of skin care products on the skin.

DISCLOSURE

Technical Problem

Conventionally, two methods have been mainly used to increase fragrance persistence on the skin. The first method is to increase the persistence of fragrance itself. The persistence was increased by adjusting the proportion of a material producing fragrance or synthesizing such a material. However, increasing the persistence of fragrance itself has a restriction on the selection of fragrance. The second method is to increase the proportion of fragrance. By increasing the proportion of fragrance in a formulation, a strong fragrance is produced from the beginning and can be maintained for a long time, but for skin care products, a fragrance proportion which is too high may cause discomfort and irritation.

Both of these methods are focused on the development of highly persistent fragrance rather than the development of a composition for increasing fragrance persistence, and thus the two methods are difficult to apply to other products.

Therefore, the present invention is intended to develop a composition capable of increasing fragrance persistence on the skin.

Technical Solution

An object of the present invention is to provide a cosmetic composition for fragrance persistence containing, as active ingredients, a non-ionic polymer having hydrophobic substituents at both termini and an oil.

Another object of the present invention is to provide a quasi-drug composition for fragrance persistence containing, as active ingredients, a non-ionic polymer having hydrophobic substituents at both termini and an oil.

Advantageous Effects

In the composition of the present invention, the non-ionic polymer having hydrophobic substituents at both termini captures an oil and fragrance by way of the hydrophobic substituent moieties thereof to form a flower micelle structure, thereby stably maintaining the fragrance and oil and preventing rapid volatilization of the fragrance, leading to an improvement in fragrance persistence.

BRIEF DESCRIPTION OF DRAWINGS

FIG. 1 shows a schematic diagram in which a non-ionic polymer having hydrophobic substituents at both termini forms a flower micelle structure.

FIG. 2 is a graph showing the results of sensory evaluation of fragrance persistence.

DETAILED DESCRIPTION OF THE INVENTION

The present invention will be specifically described as follows. Meanwhile, each description and embodiment disclosed in this present invention may also be applied to other descriptions and embodiments. That is, all combinations of various elements disclosed in this present invention fall within the scope of the present invention. Further, the scope of the present invention is not limited by the specific description below.

It could be verified through the present invention that a non-ionic polymer having hydrophobic substituents at both termini captures an oil and fragrance to form a flower micelle structure, leading to excellent uniform coating when applying to the skin, high fragrance producing power, and improved fragrance persistence, and the present invention is based on such features.

Hereinafter, the present invention will be described in detail.

An aspect of the present invention is to provide a cosmetic composition for fragrance persistence containing, as active ingredients, a non-ionic polymer having hydrophobic substituents at both termini and an oil.

As used herein, the term "non-ionic polymer having hydrophobic substituents at both termini" or "polymer" includes a tri-block copolymer, which is a hydrophilic polymer having hydrophobic groups at both termini thereof. Any tri-block copolymer having hydrophobic groups at both termini thereof may be included as long as the copolymer is known in the art and can be used for a cosmetic composition, but is not limited thereto. Specifically, at least one selected from the group consisting of PEG-150 distearate, PEG-190 distearate, PEG-250 distearate, and PEG-800 distearate, which are hydrophobically modified non-ionic polyols, may be used, and at least one selected from the group consisting of PEG-150/decyl alcohol/SMDI copolymer and PEG-150/stearyl alcohol/SMDI copolymer, which are hydrophobically modified ethoxylated urethanes, may be used. In particular, the inclusion of urethane bonds in polymer structures provides elasticity to broaden a binding site and stabilize the dispersion in formulations.

A-B-A or A-B-C [Structural Formula]

A and C: hydrophobic substituents
B: hydrophilic polymer

As used herein, the term "oil" is a concept including all oils that are typically used in cosmetic compositions.

In an embodiment of the present invention, the oil may be silicone oil, but is not limited thereto.

The silicone oil may contain fragrance or scent. The silicone oil favorably captures fragrance in formulations due to good compatibility with fragrance, so that when the polymer forms an entangled structure on the skin, the silicone oil prevents rapid volatilization of the fragrance, thereby enhancing fragrance producing power. Examples of the silicone oil may include dimethyl polysiloxane, methylphenyl polysiloxane, methyl hydrogen polysiloxane, octamethyl cyclotetrasiloxane, decamethyl cyclopentasiloxane, dodecamethyl cyclohexasiloxane, methyl trimethicone, phenyl trimethicone, dimethicone, cyclomethicone, and the like.

The cosmetic composition may have a flower micelle structure.

As used herein, the term "flower micelle structure" refers to a structure of a micelle having following features as shown in FIG. 1: a core comprising hydrophobic substituents at both termini of a non-ionic polymer having the hydrophobic substituents and an oil or an oil-phase particle; and a loop of the non-ionic polymer excluding hydrophobic substituent moieties (FIG. 1).

As used herein, the term "core" refers to a central portion of a flower micelle structure, in which hydrophobic substituent moieties from several different non-ionic polymer molecules having hydrophobic substituents at both termini form an entangled structure.

As used herein, the term "loop" may refer to a portion of a non-ionic polymer excluding hydrophobic substituent moieties, which has a structure of being bent in order to form a flower micelle structure.

As used herein, the term "micelle" refers to a structure similar to an aggregate of surfactant molecules at a predetermined concentration or higher, and is a concept in which hydrophobic portions form a nucleus and hydrophilic portions form a surface in contact with water, but is not limited thereto.

In the composition of the present invention, the non-ionic polymer having hydrophobic substituents at both termini captures an oil and fragrance to form a flower micelle structure, thereby improving fragrance persistence. The hydrophobic substituent moieties of the non-ionic polymer having hydrophobic substituents at both termini capture fragrance and an oil, wherein hydrophobic substituent moieties from several different polymer molecules form an entangled structure to generate a flower micelle structure, through which the fragrance can be stably captured.

The hydrophobic substituents in the flower micelle structures form bridges between the flower micelle structures, thereby forming a network between the flower micelle structures.

In addition, the linkage between the flower micelle structures is reversible.

Even though the intermolecular structure, while capturing fragrance and an oil, is broken by an external force, such as temperature or pressure, the intermolecular structure is re-connectable later due to the reversible structure, and thus can maintain the fragrance and oil stably.

Furthermore, the flower micelle structures are individually connected to an oil or an oil-phase particle, unlike in general polymers, leading to excellent uniform coating when applying to the skin.

The cosmetic composition may contain an entangled structure.

As used herein, the term "entangled structure" refers to a structure in which hydrophobic substituent moieties from several different non-ionic polymer molecules are entangled, and even though the intermolecular structure, while reversibly capturing fragrance and an oil by way of the hydrophobic substituent moieties through the entangled structure, is temporally broken by application of an external force, the intermolecular structure is again connected in an entangled structure when the applied external force disappears, so that the fragrance and oil can be stably maintained.

The cosmetic composition of the present invention may further contain fragrance, a fragrance ingredient, or a fragrance material that is typically used in cosmetic compositions, in addition to the non-ionic polymer having hydrophobic substituents at both termini and the oil.

As used herein, the term "fragrance", "fragrance ingredient", or "fragrance material" refers to a strongly fragrant organic material that is added to apply fragrance to daily supplies, such as cosmetic products and food products, and has superior volatility at room temperature. Fragrance materials may be classified into natural fragrance materials obtained from roses and lemons, isolated fragrance materials separated or purified from raw materials, such as natural fragrance materials or coal tar, and synthetic fragrance materials synthesized through chemical reactions. The isolated fragrance materials and synthetic fragrance materials are collectively referred to as artificial fragrance materials. Fragrance materials may be largely classified into cosmetic fragrance materials and food fragrance materials according to the purpose. Cosmetic fragrance materials are intended to apply fragrance, but food fragrance materials may be mainly directed to a flavor obtained by adding taste to smell. The fragrance, fragrance ingredient, or fragrance material of the present invention is used together with a non-ionic polymer having hydrophobic substituents at both termini to form a flower micelle structure, leading to favorable flavor capturing power and excellent fragrance producing power.

The fragrance, fragrance ingredient, or fragrance material may originate from plants or animals or may be a synthetic component, and may be an essential oil obtained by purifying fragrance ingredients from originating plants or originating animals.

The cosmetic composition according to the present invention may be prepared in a formulation selected from the group consisting of solutions, externally applied ointments, creams, foams, nutritional lotions, softening lotions, masks, softeners, milky lotions, makeup bases, essences, soaps, liquid soap, bath preparations, sunscreen creams, sun oil, suspensions, emulsions, pastes, gels, lotions, powders, surfactant-containing cleansing, oil, powder foundations, emulsion foundations, wax foundations, patches, and sprays, but is not limited thereto.

In addition, the cosmetic composition of the present invention may further contain at least one type of cosmetically acceptable carrier which is mixed in ordinary skin cosmetic materials. For example, oil, water, surfactants, humectants, lower alcohols, thickeners, chelating agents, dyes, preservatives, and fragrance materials may be appropriately mixed as a typical component, but are not limited thereto.

The cosmetically acceptable carrier contained in the cosmetic composition of the present invention may vary depending on the formulation.

In cases where the formulation of the present invention is an ointment, a paste, a cream, or a gel, animal oils, vegetable oils, waxes, paraffin, starch, tragacanth, cellulose derivatives, polyethylene glycol, silicone, bentonite, silica, talc, zinc oxide, or a mixture thereof may be used as a carrier ingredient.

In cases where the formulation of the present invention is a powder or a spray, lactose, talc, silica, aluminum hydroxide, calcium silicate, polyamide powders, or a mixture thereof may be used as a carrier ingredient, and in particular, in cases where the formulation of the present invention is a spray, the spray may further contain a propellant, such as chlorofluorohydrocarbon, propane/butane, or dimethyl ether.

In cases where the formulation of the present invention is a solution or an emulsion, solvents, solubilizers, or emulsifiers may be used as a carrier ingredient, and for example, water, ethanol, isopropanol, ethyl carbonate, ethyl acetate, benzyl alcohol, benzyl benzoate, propylene glycol, or 1,3-butyl glycol oil may be used, and in particular, cottonseed oil, peanut oil, corn germ oil, olive oil, castor oil, sesame oil, glycerol aliphatic esters, polyethylene glycol, or sorbitan fatty acid esters may be used.

In cases where the formulation of the present invention is a suspension, liquid diluents, such as water, ethanol, or propylene glycol, suspensions such as ethoxylated isostearyl alcohol, polyoxyethylene sorbitol esters, and polyoxyethylene sorbitan esters, microcrystalline cellulose, aluminum meta-hydroxide, bentonite, agar, tragacanth, or the like may be used as a carrier ingredient.

In cases where the formulation of the present invention is soap, alkali metal salts of fatty acids, salts of fatty acid hemiesters, fatty acid protein hydrolyzates, isethionates, lanolin derivatives, aliphatic alcohols, vegetable oils, glycerol, sugars, or the like may be used as a carrier ingredient.

The cosmetic composition of the present invention may further contain an adjuvant that is typically used in cosmetic compositions, for example, hydrophilic or lipophilic gelling agents, hydrophilic or lipophilic activators, preservatives, antioxidants, solvents, aromatic agents, fillers, blockers, pigments, odorants, dyes, and the like, in addition to the non-ionic polymer having hydrophobic substituents at both termini and the oil.

According to a specific exemplary embodiment, the cosmetic composition may be a cosmetic composition containing: a non-ionic polymer having hydrophobic substituents at both termini; an oil; a surfactant; purified water; glycerin; a preservative; a thickener; fragrance; and an acidity regulator, but is not limited thereto.

The non-ionic polymer of the present invention having hydrophobic substituents at both termini may be contained in a content of 0.1% to 14%, and more specifically 0.5% to 10% relative to the total weight of the cosmetic composition, but is not limited thereto.

According to a specific exemplary embodiment, the viscosity measurement of the cosmetic composition indicates that when the cosmetic composition contained the polymer, an emulsion was formed and the increase in the content of the polymer resulted in the more viscosity increase. It was also verified that when the polymer was contained in a content of 0.5% to 10%, it showed an excellent viscosity-increasing effect and was suitable for use in cosmetic compositions (Table 2).

According to another specific exemplary embodiment, it could be seen that the polymer, when contained in the composition, formed flower micelles in the composition to thereby improve stability at a high temperatures (45° C. and 50° C.), room temperature (25° C.), and a low temperature (4° C.) (Table 3).

The oil of the present invention may be contained in a content of 0.1% to 10%, and more specifically 1% to 5% relative to the total weight of the cosmetic composition, but is not limited thereto.

According to a specific exemplary embodiment, it was verified that the non-ionic polymer having hydrophobic substituents at both termini in the cosmetic composition became thickened by crosslinking with an oil-phase component, and thus an oil as the oil-phase component needs to be present in a content of 1% or more to enable polymer crosslinking.

Another aspect of the present invention is to provide a quasi-drug composition for fragrance persistence containing, as active ingredients, a non-ionic polymer having hydrophobic substituents at both termini and an oil.

As used herein, the term "quasi-drug composition" may further contain a pharmaceutically acceptable carrier, excipient, or diluent as needed. The pharmaceutically acceptable carrier, excipient, or diluent is not limited as long as it does not impair the effects of the present invention, and examples thereof may include fillers, extenders, binders, wetting agents, disintegrants, surfactants, lubricants, sweeteners, aromatic agents, preservatives, and the like.

Examples of the quasi-drug composition of the present invention may include disinfecting cleaners, shower foams, ointments, wet wipes, coating agents, and the like, and preferably, the quasi-drug composition may be prepared as semi-solid preparations, such as externally applied ointments and lotions, but are not limited thereto. The formulation methods, dosages, using methods, ingredients, and the like of the quasi-drugs may be selected as appropriate from typically used techniques known in the art.

The composition of the present invention containing a non-ionic polymer having hydrophobic substituents at both termini and an oil as active ingredients may be contained in personal care products.

In the present invention, the "personal care product" includes cosmetics, hair care products, toiletry articles, cosmeceuticals, beauty aids, insect repellents, and personal hygiene and cleansing products that are applied to the body, including skin, hair, scalp, and nails, of humans and animals, but is not limited thereto, and can be applied to all personal care compositions to which fragrance is added.

Specifically, examples of the personal care products include deodorants, antiperspirants, sprays, sticks and roll-on products, shaving products, skin lotions, moisturizers, toners, bath products, cleansing products, shampoos, conditioners, combined shampoo/conditioners, mousses, styling gels, hair sprays, hair dyes, hair colorants, hair bleaches, waving products, hair straighteners, nail polishes, nail polish removers, nail creams and lotions, cuticle softeners, sunscreens, insect repellents, anti-aging products, lipsticks, foundations, face powders, eye liners, eye shadows, blushes, makeup, mascaras, moisturizing preparations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouthwashes, massage oils, toothpastes, clear gels and sticks, ointment bases, topical wound-healing products, aerosol talc, barrier sprays, vitamin and anti-aging preparations, herbal-extract preparations, bath salts, bath and body milks, hair styling aids, hair-, eye-, nail-, and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, and nail coloring preparations, but are not limited thereto.

EXAMPLES

Example 1: Preparation of Cosmetic Composition Containing Non-Ionic Polymer Having Hydrophobic Substituents at Both Termini Dimethicone, hexyldecyl ethylhexanoate, squalane, neopentyl glycol dicaprate, PEG-40 stearate, sorbitan stearate, glyceryl stearate, PEG-100 stearate, and cetearyl alcohol were weighed and then dissolved and dispersed at a high temperature. Thereafter, purified water, glycerin, trisodium EDTA, 1,2-hexanediol, carbomer, acrylate/C10-30 alkyl acrylate cross-polymer, and PEG-150/decyl alcohol/SMDI copolymer were weighed, and then stirred by a disper at room temperature, and mixed and stirred at high temperature. Thereafter, the materials that were dissolved and dispersed at the high temperature were added thereto, followed by emulsification, and then fragrance was added thereto, followed by neutralization with tromethamine.

Experimental Examples 1 to 4, and Comparative Examples 1 and 2 were grouped by varying the amount of the non-ionic polymer having hydrophobic substituents at both termini (PEG-150/decyl alcohol/SMDI copolymer) among the materials for the cosmetic composition, and subjected to comparison experiments. The contents of respective ingredients of each cosmetic composition are shown in Table 1.

TABLE 1

| Ingredient name | Experimental Example 1 | Experimental Example 2 | Experimental Example 3 | Experimental Example 4 | Comparative Example 1 | Comparative Example 2 |
|---|---|---|---|---|---|---|
| Dimethicone | 1 | 1 | 1 | 1 | 1 | 1 |
| Hexyldecyl ethylhexanoate | 2 | 2 | 2 | 2 | 2 | 2 |
| Squalane | 1 | 1 | 1 | 1 | 1 | 1 |
| Neopentyl glycol dicaprate | 1 | 1 | 1 | 1 | 1 | 1 |
| PEG-40 stearate | 0.5 | 0.5 | 0.5 | 0.5 | 0.5 | 0.5 |
| Sorbitan stearate | 0.3 | 0.3 | 0.3 | 0.3 | 0.3 | 0.3 |
| Glyceryl stearate, PEG-100 stearate | 0.5 | 0.5 | 0.5 | 0.5 | 0.5 | 0.5 |
| Cetearyl alcohol | 0.3 | 0.3 | 0.3 | 0.3 | 0.3 | 0.3 |
| $C_{14-22}$ alcohol, $C_{12-20}$ alkyl glucoside | 0.5 | 0.5 | 0.5 | 0.5 | 0.5 | 0.5 |
| Purified water | 58.98 | 57.48 | 54.48 | 49.48 | 59.48 | 44.48 |
| Glycerin | 1 | 1 | 1 | 1 | 1 | 1 |
| Trisodium EDTA | 0.02 | 0.02 | 0.02 | 0.02 | 0.02 | 0.02 |
| 1,2-Hexandiol | 2 | 2 | 2 | 2 | 2 | 2 |
| Purified water | 30 | 30 | 30 | 30 | 30 | 30 |
| Carbomer | 0.07 | 0.07 | 0.07 | 0.07 | 0.07 | 0.07 |
| Acrylate/$C_{10-30}$ alkyl acrylate cross-polymer | 0.05 | 0.05 | 0.05 | 0.05 | 0.05 | 0.05 |

TABLE 1-continued

| Ingredient name | Experimental Example 1 | Experimental Example 2 | Experimental Example 3 | Experimental Example 4 | Comparative Example 1 | Comparative Example 2 |
|---|---|---|---|---|---|---|
| PEG-150/decyl alcohol/SMDI copolymer | 0.5 | 2 | 5 | 10 | — | 15 |
| Fragrance | 0.18 | 0.18 | 0.18 | 0.18 | 0.18 | 0.18 |
| Tromethamine | 0.1 | 0.1 | 0.1 | 0.1 | 0.1 | 0.1 |

Example 2: Measurement of Viscosity Depending on Content of Non-Ionic Polymer Having Hydrophobic Substituents at Both Termini Experiments were carried out by using the PEG-150/decyl alcohol/SMDI copolymer as a hydrophobically modified ethoxylated urethane (HEUR) polymer, which pertain to one type of non-ionic polymers having hydrophobic substituents at both termini. The PEG-150/decyl alcohol/SMDI copolymer was added in contents of 0.5%, 2%, 5%, and 10% relative to the total weight of the cosmetic composition in Experimental Examples 1 to 4, respectively. The PEG-150/decyl alcohol/SMDI copolymer was not included in Comparative Example 1, and was added in a content of 15% in Comparative Example 2.

As a result, Comparative Example 1 with the polymer not included showed the formation of a low-viscosity emulsion, and Comparative Example 2 with 15% or more of the polymer added showed a change into a cream phase due to a high content of the polymer, making it impossible to measure the viscosity thereof.

It can be seen that in all of Experimental Examples 1 to 4, an emulsion was formed and the viscosity increased with the increase of the content (Table 2).

It was verified through the experiment that only when the content of the polymer is at least 0.5%, the polymer became thickened while crosslinking with an oil as an oil-phase component, thereby providing a viscosity-increasing effect; and a polymer content of 0.5% to 10% can offer a feeling of use suitable for cosmetic use while still providing a viscosity-increasing effect.

TABLE 2

| | Experimental Example 1 | Experimental Example 2 | Experimental Example 3 | Experimental Example 4 | Comparative Example 1 | Comparative Example 2 |
|---|---|---|---|---|---|---|
| Viscosity | 2700 | 6660 | 7820 | 18080 | 2340 | — |

Example 3: Measurement of Formulation Stability Depending on Content of Non-Ionic Polymer Having Hydrophobic Substituents at Both Termini To investigate how the polymer content affects formulation stability, stability tests were conducted at room temperature (25° C.), high temperatures (45° C., 50° C., CYC), and at a low temperature (0° C.).

Comparative Example 1 with the polymer not included showed inferior stability at the high temperatures. However, Experimental Example 1 with the polymer added showed improved stability at temperatures except 50° C., and Experimental Examples 2, 3, and 4 showed improved stability at all of the temperatures. Comparative Example 2 with a high content of polymer added showed the formation of an elastic gel at the low temperature, but the elasticity actually disappeared and the gel broke, resulting in reduced stability. It could be verified through the experiment that the stability increases in the use of the polymer rather than the non-use of the polymer, but the use of 15% or more of the polymer actually results in deterioration in stability (Table 3).

TABLE 3

| | Experimental Example 1 | Experimental Example 2 | Experimental Example 3 | Experimental Example 4 | Comparative Example 1 | Comparative Example 2 |
|---|---|---|---|---|---|---|
| Room temperature (25° C.) | ○ | ○ | ○ | ○ | ○ | ○ |
| 45° C. | ○ | ○ | ○ | ○ | ○ | ○ |
| 50° C. | Δ | ○ | ○ | ○ | Δ | ○ |
| Cycle | ○ | ○ | ○ | ○ | Δ | ○ |
| 4° C. | ○ | ○ | ○ | ○ | ○ | Δ |

Example 4: Sensory Evaluation of Fragrance Persistence

After eleven men and women were divided into a control group and an experimental group, each of the cosmetic compositions was applied to the inner parts of both arms of each person, and then sensory evaluation with respect to fragrance intensity over time was conducted. The composition of Comparative Example 1 with the polymer not included was used for the control group, and the composition of Experimental Example 2 with 2% of the polymer added was used for the experimental group (see Table 1).

The intensity of fragrance was evaluated with a score of 0 to 5 immediately after applying each cosmetic composition at 0.25, 0.5, 1, 2, 4, 6, and 8 hours. The results are as shown in FIG. 2.

As a result of the experiment, the fragrance intensity of each cosmetic composition was similar at the time of applying the same, but after 1 hour, the fragrance intensity rapidly decreased in the control group. The fragrance intensity gradually decreased over time in the experimental group. In particular, the fragrance intensity after 2 hours in the control group was 1.73, which was similar to the value after 4 hours in the experimental group. After 8 hours, the average values in both the experimental group and the control group were close to 0, but more than half of the subjects in the experimental group evaluated the fragrance as remaining (>0).

It could be verified through the above experiment that the experimental group using a non-ionic polymer having hydrophobic substituents at both termini showed higher fragrance persistence.

While the present invention has been described with reference to the particular illustrative embodiments, a person skilled in the art to which the present invention pertains can understand that the present invention may be embodied in other specific forms without departing from the technical spirit or essential characteristics thereof. Therefore, the embodiments described above should be construed as being examples and not limiting the present invention. The scope of the present invention is not defined by the detailed description as set forth above but by the accompanying claims of the invention, and it should also be understood that all changes or modifications derived from the definitions and scopes of the claims and their equivalents fall within the scope of the invention.

The invention claimed is:

1. A method for improving fragrance persistence comprising: applying a cosmetic composition comprising a non-ionic polymer having hydrophobic substituents at both termini, an oil and a fragrance, as active ingredients,
   wherein the oil is dimethicone,
   wherein the content of the non-ionic polymer having hydrophobic substituents at both termini is 2% to 10% by weight relative to the total weight of the cosmetic composition,
   wherein the non-ionic polymer having hydrophobic substituents at both termini is PEG-150/decyl alcohol/SMDI copolymer, and
   wherein the oil, the fragrance, and the non-ionic polymer having hydrophobic substituents at both termini form a flower micelle structure in the cosmetic composition by the oil and the fragrance being captured by the hydrophobic substituents of the non-ionic polymer, and thereby improving fragrance persistence,
   and wherein the cosmetic composition further comprises water in an amount ranging from 74.48% to 89.48% relative to the total weight of the cosmetic composition.

2. The method of claim 1, wherein the content of the oil is 0.1% to 10% relative to the total weight of the cosmetic composition.

3. The method of claim 1, wherein the content of the oil is 1% to 5% relative to the total weight of the cosmetic composition.

4. The method of claim 1, wherein the hydrophobic substituents at both termini are hydrophobic substituents of different non-ionic polymer molecules, and the hydrophobic substituents form an entangled structure.

5. The method of claim 1, wherein the flower micelle structure comprises: a core comprising the hydrophobic substituents at both termini and the oil; and a loop of the non-ionic polymer excluding the hydrophobic substituents.

* * * * *